United States Patent [19]

Modrovich

[11] 4,250,254

[45] Feb. 10, 1981

[54] STABILIZED LIQUID ENZYME AND COENZYME COMPOSITIONS

[76] Inventor: Ivan E. Modrovich, 1043 Mesa Dr., Camarillo, Calif. 93010

[21] Appl. No.: 940,941

[22] Filed: Sep. 11, 1978

Related U.S. Application Data

[63] Continuation of Ser. No. 722,565, Sep. 13, 1976, abandoned.

[51] Int. Cl.³ .................... C12Q 1/54; C12Q 1/50; C12N 9/96
[52] U.S. Cl. .................... 435/14; 435/17; 435/21; 435/26; 435/188; 435/190; 435/194
[58] Field of Search ............... 435/14, 17, 188

[56] References Cited

U.S. PATENT DOCUMENTS

| | | | |
|---|---|---|---|
| 3,539,450 | 11/1970 | Deutsch | 435/188 |
| 3,540,984 | 11/1970 | Deutsch | 435/15 |
| 3,557,002 | 1/1971 | McCarty | 435/188 X |
| 3,627,688 | 12/1971 | McCarty et al. | 435/188 X |
| 3,721,607 | 3/1973 | Gruber et al. | 435/14 |
| 3,761,420 | 9/1973 | Bogardus | 435/188 X |
| 3,764,478 | 10/1973 | Bergmeyer et al. | 435/4 |
| 3,776,900 | 12/1973 | Hammer | 435/26 X |
| 3,778,350 | 12/1973 | Bergmeyer et al. | 435/14 |

OTHER PUBLICATIONS

George, et al., Stabilization of Lactose and Malate Dehydrogenase By Organic Solvents, Biochem., Biophys. Acta., vol. 191, 1969 pp. 466-468.

*Primary Examiner*—David M. Naff
*Attorney, Agent, or Firm*—Romney, Schaap, Golant, Disner & Ashen

[57] ABSTRACT

Stabilized liquid enzyme and/or coenzyme compositions are prepared for use in biological diagnostic determinations. The compositions contain an enzyme and/or coenzyme, an organic solvent such as a polyol and an aqueous vehicle. The compositions may also contain a polymer and a bacteriostat. The compositions exhibit excellent shelf life and the container in which a composition is stored can be repeatedly opened for use without any substantial degradation of the enzyme and/or coenzyme.

67 Claims, No Drawings

STABILIZED LIQUID ENZYME AND COENZYME COMPOSITIONS

RELATED APPLICATION

This application is a continuation of Application Ser. No. 722,565, filed Sept. 13, 1976 for STABILIZED LIQUID ENZYME AND COENZYME COMPOSITIONS AND METHOD OF PREPARING SAME (now abandoned).

BACKGROUND OF THE INVENTION

I. Field of the Invention

This invention relates in general to certain new and useful improvements in the stabilization of enzymes and coenzymes and the method of stabilizing, and, more particularly, to stabilized labile enzymes and coenzymes in a single aqueous organic solvent media.

II. Description of the Prior Art

It has recently been estimated that 25% of all in vitro diagnostic tests conducted annually in this country are not reliable. Unreliable tests can result in unnecessary medical treatment, the withholding of necessary treatment and lost income. Because of their high specificity, the use of enzyme determinations has significantly increased during the last few years and indications are that this trend will continue. However, rigorous quality control measures are required to assure the accuracy and consistency of results. This requirement stems from the fact that the exact nature of enzymes, as well as the mechanisms of their action, remains unknown for the most part.

At present, the greatest limitation on the enzyme reagent manufacturer, by far, lies in the unstable characteristics of his products. Current methodologies require the use of numerous labile ingredients, and these ingredients are more likely to increase, rather than decrease, in number. Due to these severe restraints, rigorous quality control is required, and this quality control is, of course, costly. Moreover, if control in any step in the process is not maintained within high degree of control standards, the quality of the final product can be reduced materially.

The present commercial state of the art used for stabilizing the reactive ability of enzymes or coenzymes is by locking them into a solid matrix, either by freeze drying, dry blending such as used for tableting dried powders, primarily in the pharmaceutical diagnostic and related industries and immobilization by locking the chemical structure of the enzyme into a solid matrix. Contrary to the sophistication there terms imply, these approaches are neither practical nor desirable and are also expensive. The manufacturer is forced to remove the water and supply a partial product, thus relinquishing part of the quality control cycle in the dilution and use of the final product. Laboratories are forced to pay the high cost of packaging, reagent waste, freeze drying and dry blending, and usefulness of the product is further limited by packaging modes and sizes.

Furthermore, good product uniformity is difficult to achieve. This condition is exemplified by the fact that most commercial freeze dried control sera (reference serum) list the acceptable bottle-to-bottle variation of enzyme constituents at ±10% of the mean.

The present invention is uniquely designed so that the labile ingredients in a liquid enzyme solution are effectively "stabilized" by controlling the activity of the active sites of the enzyme and stabilizing a liquid coenzyme solution against reactivity. Both enzymes and coenzymes may be stabilized in the same solution. This means of stabilization ensures long-term stability in a liquid media. Moreover, close tolerance control can be achieved in the manufacturing of a high quality product which eliminates the inconvenience of the rigid package size and the high cost of packaging and freeze drying and reagent waste.

OBJECTS OF THE INVENTION

It is, therefore, the primary object of the present invention to provide a liquid composition with coenzymes and/or enzymes which are stabilized in a single container.

It is an additional object of the present invention to provide a stabilized composition of the type stated in a single container which has excellent shelf life and which container may be repeatedly opened without substantial degradation of the labile components therein.

It is another object of the present invention to provide a labile coenzyme which may be stored in a liquid media, in the presence of another coenzyme an/or other labile enzymes, and all of which are stabilized against degradation.

It is a further object of the present invention to provide a labile enzyme and coenzyme composition of the type stated in an aqueous organic solvent media and where the stabilization of the enzyme and coenzyme does not affect the enzymatic reactivity after a substantial period of time.

It is also an object of the present invention to provide a method of stabilizing labile enzymes and/or coenzymes in a liquid media with relatively low-cost, commercially available stabilizing ingredients.

It is another salient object of the present invention to provide a method of stabilizing labile enzymes and/or coenzymes in the presence of other labile coenzymes or otherwise other labile enzymes and which composition has a long shelf life.

It is yet another object of the present invention to provide a method of stabilizing enzymes and/or coenzymes in the presence of a liquid media for a substantial period of time at a relatively and with a high degree of composition purity.

With the above and other objects in view, my invention resides in the novel compositions and the methods of making the same as hereinafter described in more detail.

SUMMARY OF THE INVENTION

Labile enzymes and coenzymes are treated according to the invention, resulting in long-term stability without affecting enzymatic or coenzymatic reactivity or phometric absorptivity. The invention provides reagents where quality control is assured throughout manufacturing, packaging, storage and use. The inconvenience of rigid package size is eliminated as is the high cost of packaging, freeze drying and reagent waste. Liquid enzyme and coenzyme systems provide application flexibility and separation of the ingredients is easily accomplished with negligible manufacturing cost providing the flexibility of triggering the desired reaction after all side reactions have been dissipated.

The stabilized enzymes and coenzymes of the invention have been assessed in studies which compared respective liquid enzyme and liquid coenzyme reagents with fresh reagents. The studies show a 1:1 correlation between aged liquid and fresh reagents with comparable sensitivity and precision. Providing enzyme and coenzyme reagents in a stable liquid form enhances the coloimetric applicability of present day NAD/NADH coupled methodologies, as well as other methodologies, primarily because the separation of ingredients is easily accomplished. Stable liquid reagents are especially advantageous where NADH and other coenzyme consumption is the basis of measurement and the color reagent must be separated from NADH and the reaction main. In the ultraviolet mode, the liquid system offers better reagent homogeneity and packaging, as well as flexibility in usage, in contrast to the freeze-dried or dry media preparations.

In diagnostic enzymology, the stabilization of enzyme and coenzyme reagents in a ready-to-use liquid media is a new and exciting approach to satisfy the needs of the clinical laboratory and the reliability demands of the regulatory authorities. The flexibility of liquid enzyme and coenzyme systems ensures their applicability to automated instrumentation, as well as their convenience in manual testings.

The liquid media which is designed to provide for stabilization of enzymes and coenzymes as hereinafter described is uniquely formulated so that one or more coenzymes may be stabilized in the media. Otherwise, one or more enzymes may be stabilized in the liquid media. Moreover, both coenzymes and enzymes may be stabilized in the same liquid media in a single container.

Stabilization of the enzymes and/or coenzymes is accomplished by dissolving a polymer, such as a gelatin, in distilled water. The gelatin is preferably dissolved on a 0.1% w/w basis. Thereafter, the solubilized gelatin in water is heated to about 30° to fully dissolve the gelatin. In some cases, an azide compound may be used, which not only serves as a bacteriostat, but as a stabilizer as well. Thereafter, this solution is cooled down essentially to room temperature, or about 20° C.

In one case, the coenzyme, nicotinamide-adenine dinucleotide (NAD), is added to the solution, along with a buffering agent, such as tris(hydroxymethyl)aminomethane, for purposes of adjusting the pH. In this case, the pH is adjusted approximately between about 6.0 to about 8.5 with a preferred pH of 7.5. After the addition of the coenzyme, a polyol, such as glycerol, is added on about a 30% v/v basis. After addition of the polyol, the pH may again be adjusted to about 7.5.

In accordance with the present invention, more than one coenzyme may be stabilized in the above-mentioned solution. In this case, the other of the coenzymes could be added prior to or after the addition of the NAD. For example, in one embodiment of the present invention, adenosine triphosphate (ATP) may be added as the other coenzyme.

After the addition of the coenzymes and the adjustment of the pH of the liquid, an enzyme, such as hexokinase (HK), may also be added. Typically, the hexokinase would be added from a suspension, such as a glycerol suspension, or an ammonium sulfate suspension. Another enzyme may also be added, as for example, glucose-6-phosphate dehydrogenase.

After the liquid stabilized enzyme and/or coenzyme solution is prepared, it is then dispensed into amber-glass bottles and which are sealed in an air-tight condition. Moreover, these bottles are typically stored under refrigeration. The projected shelf life of the stabilized enzymes and coenzymes is up to four years under these conditions without appreciable degradation.

It has been found in accordance with the present invention that the enzymes and coenzymes exhibit good solubility and stability in the aqueous miscible organic solvent. The envisioned chemical or physical reaction which provides for the stabilization of the enzymes and coenzymes is more fully described hereinafter.

These and other features and attendant advantages of the invention will become apparent as the invention becomes better understood by reference to the following general description and the following detailed description.

DETAILED DESCRIPTION

In the clinical diagnostic field, the commercial application of the present invention is represented by, but not limited to, the diagnostic reagents used to determine substrate concentration, as for example, glucose concentrations in biological fluids, and the like. Nevertheless, compositions prepared in accordance with the present invention can be used to determine and quantitate other biological constituents, as for example, the following constituents in biological fluids:

1. Glutamic-oxalacetic transaminase (SGOT)
2. Glutamic-pyruvic transaminase (SGPT)
3. Lactic dehydrogenase (LDH-P)
4. Lactic dehydrogenase (LDH-L)
5. Creatine Phosphokinase (CPK)
6. α-Hydroybuteric dehydrogenase (α-HBD)
7. Glucose (via Hexokinase-G-H-PDH)

These above-identified reagents often react similarly, contain some common labile ingredients, and some of the chemical reactions involved are common. The following chemical reaction scheme is presented as a model to illustrate the general nature of the reactions involved:

REACTION SCHEME 1 -- GENERAL MODEL

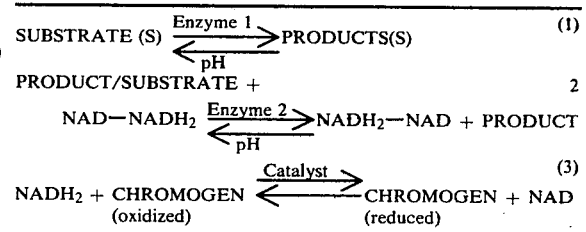

All enzymatic reactions listed above, in accordance with this invention, will follow this general scheme, where reaction (2) is usually referred to as the coupling reaction, reactions (2) or (3) are the measuring reactions, and reaction (1) may be characterized as the primary reaction. It is understood, however, that not all three reactions are required for measurement; in fact, they may be limited to two, or one. In the case of the ultraviolet measurement of lactic dehydrogenase (LD) activity, only reaction (2) is involved, as follows:

REACTION SCHEME 2—LDH

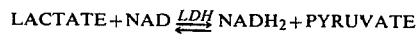

Conversely, more than the three reactions listed may be involved, as in the case of Creatine phosphokinase (CPK):

REACTION SCHEME 3—CPK $$GP + ADP \underset{}{\overset{CPK}{\rightleftharpoons}} ATP + CREATINE \quad (1)$$

$$ATP + GLUCOSE \underset{}{\overset{HK}{\rightleftharpoons}} GLUCOSE\text{-}6\text{-}PHOS. + ADP \quad (2)$$

$$GLUCOSE\text{-}6\text{-}PHOS. + NAD \underset{}{\overset{G\text{-}6\text{-}PDH}{\rightleftharpoons}} NADH_2 \quad (3)$$

$$NADH_2 + INT \underset{(ox)}{\overset{PMS}{\underset{\longleftarrow}{\longrightarrow}}} INT + NAD \quad (4)$$
$$\hspace{3em} (red)$$

SYMBOLS

CP = Creatine phosphate
CPK = Creatine phosphokinase
ADP = Adenosine-5'-diphosphate
AM = Adenosine monophosphate
ATP = Adenosine triphosphate
HK = Hexokinase
NAD = Nicotinamide-adenine dinucleotide
NADP = Nicotinamide-adenine dinucleotide phosphate
$NADH_2$ = Nicotinamide-adenine dinucleotide, reduced
GLDH = Glutamate dehydrogenase
G-6-PDH = Glucose-6-phosphate dehydrogenase
G-6-P = Glucose-6-phosphate
INT = Tetrazolium salt
PEP = Phosphoenol pyruvate
PMS = Phenazine methosulfate
PK = Pyruvate kinase In this case, reactions (2) and (3) may be considered the coupling reactions, reactions (3) or (4) the measuring reactions, and reaction (1) the primary reaction.

Referring to REACTION SCHEME 1—GENERAL MODEL, it becomes obvious and is general knowledge that the use of the reaction sequence permits the analytical quantitation of either the reaction substrates/products or the catalyzing enzymes.

The quantitation of these constituents in biological fluids is a well accepted and widely used diagnostic tool in diagnosis and treatment of human and animal disease states.

Enzymes are large molecular weight, complex protein molecules, usually of unknown chemical structure. They are presently classified by their catalytic activity and extreme substrate specificity. Enzymes may be redefined as biological catalysts, capable of catalyzing a reaction of a single substrate, or a reaction of a similar group of substrates.

Coenzymes are lower molecular weight organic chemicals of well-defined structure, whose reactions or interactions are necessary for specific enzyme assay or reaction. The coenzymes are catalyzed by the enzymes resulting in a reversible change in the coenzyme's structure and/or atomic composition. Coenzymes are very useful in clinical assay procedure. Some have strong absorbance, their reactions are stiochiometric with the substrate and, therefore, the creation or disappearance of the absorbing form can be followed photometrically. Nicotinamide-adenine dinucleotide (NAD) and its reduced form ($NADH_2$) are used in many important clinical assays such as the S.G.O.T, S/P.G.T. and LDH assays previously described. NAD and $NADH_2$ have a molecular weight of about 700 and are very complex organic molecules. $NADH_2$ absorbs strongly at 340 nm, whereas NAD does not absorb at this wave length.

Substrates are organic chemicals of known structure, whose reactions or interactions are catalyzed by enzymes resulting in a change in the compound's structure, atomic composition, or stereo-chemical rotation. In general, substrates are prone to microbiological degradation as they serve as food for bacteria, fungi, and other microorganisms. Otherwise, these compounds remain stable in aqueous media at or near neutral pH (I.e., pH range of 4-10). Typical substrates are glucose, lactate or lactic acid, gluconate and the like.

The following reactions illustrate the determination of glucose by utilization of the coenzymes ATP and NAD.

$$GLUCOSE + ATP \underset{}{\overset{HK}{\rightleftharpoons}} G\text{-}6\text{-}P + ADP$$

$$G\text{-}6\text{-}P + NAD \underset{}{\overset{G\text{-}6\text{-}PDH}{\rightleftharpoons}} NADH + 6\text{-}PHOSPHOGLUCONIC\ ACID$$

The enzyme which causes the primary reaction is hexokinase, and the enzyme which causes the coupling and measuring reaction is G-6-PDH. In the above reaction, the glucose is determined by measuring the NADH which is formed in the measuring reaction. In essence, the reaction is permitted to go to completion, and the amount of the coenzyme NADH formed is essentially measured.

NAD, while being unstable in water and in dry form when exposed to humid environments, is not nearly as unstable as the reduced from $NADH_2$. Accordingly, the $NADH_2$ must be kept free of moisture, whereas the NAD may be packaged in a container with an aqueous solution, although stabilized in accordance with the present invention. Stability is better in an acid pH, whereas in an alkaline pH, there is a tendency for the NAD to decompose. Neither the exact mechanism, nor the end products, are of significance, except that the decomposed NAD can no longer effectively function as a coenzyme, nor does it necessarily possess the extenction coefficient at the necessary wave length.

The compounds ADP, ATP and AMP are chemically in the form of nucleotides. However, these compounds AMP and ADP and ATP are often referred to herein as coenzymes or cofactors even though they are classifically nucleotides. Thus, the ADP, ATP and AMP will be referred to as coenzymes or cofactors herein to conform to nomenclature often used for these compounds and since they do in fact constitute an integral and important part of a coenzyme structure.

One of the unique advantages of the present invention is that all components may be stabilized in a single reagent bottle. Generally, there are two primary considerations in the formulation of a stabilized enzyme or coenzyme. The first of these considerations is that of providing a highly stable enzyme or coenzyme in a liquid media, and the second consideration is to limit the number of packages as much as possible. In the stabilization of coenzymes, such as NAD, it has been observed that the NAD is far more stable than the NADH. Consequently, it is not necessary to use the complex stabilization techniques necessary for NADH. Accordingly, all reagents can be packaged in one solution.

In stabilizing the enzymes and coenzymes of the present invention, a polymer, such as a gelatin, is dissolved in distilled water. The polymer is preferably present in the stabilized solution up to an amount that remains in homogeneous suspension under refrigeration without precipitation. The polymer should be present in an amount at least about 0.01% and normally from about 0.01% to about 0.5% based on the total composition, and preferably within a range of 0.05% to about 0.25%. Any water-soluble polymers which are useful as stabilizing agents in this invention are those which do not inhibit enzymatic activity and are capable of entrapping the enzyme in the polymer matrix. The polymer may be a synthetic or organic material, such as polyvinylpyrrolidine or dextran of biologic orgin, such as gelatin which is denatured collagen.

The polymer may be dissolved in the water by heating, generally to above 30° C. The rate in which the polymer is dissolved will increase with an increase in temperature.

After the polymer has been completely dissolved in water, an azide compound, such as sodium azide, may be added, preferably in amount of about 0.1% w/w. However, the amount of azide compound which is added can range from 0.01% to about 0.5%. It has been found in accordance with the present invention that the azide compound exhibits the rather surprising result of aiding in the stability of the enzymes. Previously, it was only thought that the azide compound served as a bacteriostatic agent. Nevertheless, while the complete mechanism of stabilization with the azide compound, in combination with the other ingredients, is not fully understood, it has been established that the azide compound does, nevertheless, provide increased stability. In many cases, the azide salt is not necessary and can be eliminated. Thus, in many cases, the polymer and organic solvent in the aqueous media are sufficient to provide the required stabilization of the labile components. In some few cases, the azide salt must be eliminated inasmuch as it may have a tendency to interefere with stabilization, or otherwise materially affect a substrate, as for example, glucose.

In addition to the foregoing, other bactericidal or other fungicidal agents which do not chemically react with a substrate or inhibit the enzymatic reaction may be employed. For example, some of these agents which may be used in addition to sodium azide are benzoic acid, phenol, thymol or pentachlorophenol.

In some cases, it may be desirable to employ a metal, such as magnesium, which aids in initiation of a reaction when the stabilized composition is used. Magnesium, in the salt form of magnesium chloride is one of the preferred agents for this purpose. This agent does not have to be incorporated in the stabilized compositions of the present invention and if used, it may be added at the time of use or incorporated during preparation. This agent which activates the coupling enzymes should be used in an amount of about 0.1% to about 1% and preferably about 0.03%.

At this point in the process, the solution may be cooled to about room temperature, such as about 20° C. to about 25° C. in a water bath. After the solution has been cooled, a buffering agent, such as tris(hydroxymethyl)aminomethane may be added. Typically, this buffering agent is added in an amount of about 50 millimoles to about 200 millimoles, but at least sufficient to maintain the pH within a range of 6.0 to about 8.5. Other known buffering agents and other forms of buffering agents may also be employed in the process. In some cases, buffer salts of the type hereinafter described may be used. The buffer salt is added in an amount necessary to maintain the pH between 6.0 to 8.5. Generally, the buffer is a combination of 0.1–1% of an alkali metal hydroxide and 0.5 to 3% of an alkali metal acid carbonate or phosphate. The total salt content also effects the amount of polymer required. At higher salt content, e.g. above 4% by weight, less polymer is required due to the electrostatic stabilization provided by the salt. However, at higher salt content, the polymer may cloud the solution or precipitate requiring warming the solution to redissolve.

After the pH of the solution has been adjusted to the desired range, the first of the coenzymes, such as the ATP or the NAD, etc., may be added. In this case, the ATP is added on a basis of about 0.3 millimoles to about 30 millimoles, based on the total composition.

As indicated previously, it is possible to form solutions of both stabilized enzymes and coenzymes. Thus, two or more coenzymes and two or more enzymes may be stabilized in the same solution. For example, the coenzyme ATP may be stabilized in the manner as described herein. On the other hand, the NAD may also be stabilized individually in the manner as described herein. Nevertheless, when stabilizing two or more coenzymes, the coenzymes may generally be added simultaneously or in any order. The NAD is preferably added in a range of about 0.6 millimole to about 60 millimoles, based on the total composition.

At this point in the process, the pH should again be adjusted to at least within the range of 6.5 to about 8.0 or less, and, preferably, to 7.5.

After adjustment of the pH, a suitable organic solvent, such as glycercol, may be added. In this case, it is added within the range of 25% to 40% v/v, although, in the most preferred aspect, at least 30% v/v of the organic solvent is added. However, the amount of organic solvent should be at least 5% v/v and could range from about 5% to 70% v/v.

The organic solvent should have the following characteristics:
1. pH range of 4 to 10;
2. Liquid at room and refrigerator temperatures;
3. Does not react with NAD or ATP and the like other than forming electrostatic (i.e., hydrogen) bonds;
4. miscible with water;
5. Standard free energy of solvolysis is low (normal resonance is established).

The solvent must be miscible with water, liquid at room and refrigerator temperatures, and non-degradatively reactive with reactive sites of the enzymes and coenzymes other than formation of electrostatic bonds. Useful solvents are generally stable organic solvents such as ethers, ketones, sulfones, sulfoxides and alcohols such as methanol, ethanol, propanel, butanol, acetone, dioxane, DMSO, dimethylsulfone and THF. However, higher activity at lower solvent concentration for the treatment step is found for liquid polyol solvents. Liquid polyols containing from 2–4 hydroxyl groups and 2–10 carbon atoms are preferred, such as glycerol, ethylene glycol, propylene glycol or butane diol. Glycerol, propylene glycol, 1,2-propanediol, were found to possess all these qualities and are the solvents of choice.

When the selected organic solvent is a polyol, it is not necessary to use the azide compound, or, for that matter, other bacteriostatic agents, since the polyol effectively functions as a bacteriostatic agent. Nevertheless, while the selected solvent and the polymer provide the required stability in an aqueous solution, the azide compound is sometimes preferable, inasmuch as it appears to increase the coupling between the polymer and the enzymes.

After the glycerol or other polyol is added, the pH of the solution thus formed is readjusted. Typically, the pH may be slightly basic and, therefore, a 1 normal HCl can be added in order to adjust the pH. In like manner, if the pH is slightly acidic, then a suitable base may be added to achieve a pH of 7.5.

One of the important aspects is that the coenzyme NAD is present in excessive amounts. As indicated, the determination of glucose is accomplished by measuring the NADH which is formed from the NAD. The NADH is unstable in an acidic environment and will degrade at a pH of 6 and, even moreso, will degrade extremely rapidly at a pH of 4. The pH of the solution is therefore maintained above a neutral pH of 7. While the NAD is actually more stable in the acid environment, it has been found in accordance with the present invention that it does not materially degrade in a slightly basic environment of a pH of 7.5. Nevertheless, the NAD is added in considerable excess so that there is always sufficient undegraded NAD present, even after several years in this liquid environment.

Generally, all coenzymes will be present in an amount at least sufficient to perform the desired determination. There is typically no maximum amount of coenzyme present, although the maximum amount will be limited by commercial practicalities and considerations of coenzyme inhibition of an assay. However, in all cases, the minimum and maximum amount of the coenzyme present will be predicated on the requirements for stability and long shelf life in the stabilized liquid environment.

After the coenzymes have been added to the liquid solution, the selected enzymes may be added. As with the case of the coenzymes, the enzymes may be added in any order. Again, one or more enzymes may be added to the solution. In the preferred aspect of the invention, and in accordance with the enzyme system identified above, the two enzymes are HK and G-6-PDH. The HK is also preferably added in no less than 100 IU per liter (pH of 7.6, 25° C.). However, it is preferable to add at least 1,000 IU per liter of the HK.

The G-6-PDH should, preferably, be formed from the L-mesenteroides bacteria, and should be concentrated in a range of about 100 IU per liter to about 30,000 IU per liter or above. In the preferred aspect of the invention, it is normally about 3,000 IU of the G-6-PDH of this type which is used at a pH of about 7.8 at 25° C.

The enzymes should each be present in an amount of at least 100 IU (International Units) per liter, although in most commercial reagents, the enzyme, as for example, the hexokinase, should be present at about a minimum of 1,000 IU per liter. In the normal commercial packages, the enzyme is present in about 1,000 to about 10,000 IU at a pH of 7.6 and at a temperature of about 25° C. However, the maximum amount of the enzyme is unlimited, although, normally, in almost all applications the amount of enzyme will not exceed 100,000 IU.

It is important in the process of the present invention that the enzymes are added after the final pH is adjusted. While the full mechanism for accomplishing the stabilization of the enzymes and coenzymes is not fully understood, it is believed that the selected solvent stabilizes the enzyme in the liquid media by protecting the functional group site, that is the part of the molecule where a substrate reaction may actually occur, or is otherwise catalyzed. Moreover, stabilization is believed to occur by protecting the enzymes and coenzymes from microbial contamination and thus degradation. The coenzyme NAD differs from the coenzyme NADH in that the NAD will not appreciably dissolve in the selected solvent, such as propyleneglycol. However, the NAD is more stable in water and the coenzyme does appear to be stabilized by the polyol. A pure polyol will denature the enzymes, but in the presence of an aqueous solution, such as a water-solvent mixture, the enzymes do not denature. Apparently, a polar group is required in the organic solvent to maintain the active sites of the enzymes in a stable condition. Obviously, some form of physical or chemical reaction occurs in the concentrated aqueous-organic solvent media, inasmuch as the enzymes and coenzymes retain catalytic activity and do not degrade in the specified concentrations.

In addition to the above, the polymer appears to react in some fashion with the azide compound in order to form an electrostatic or covalent bond between the enzymes and the polymer. In essence, it may also appear that the polymer may stretch to somewhat encapsulate, and thereby protect, the active sites of the enzymes. In this way, enzyme denaturation or other form of degradation is inhibited or does not occur.

As indicated above it is possible to stabilize at least two or more encoenzymes or at least two or more enzymes in the same solution. Moreover, and more importantly, it is possible to stabilize both enzymes and coenzymes in the same solution. It is believed that the aqueous solution of the organic solvent is the primary factor in stabilizing the coenzyme although the polymer does appear to provide some stabilizing effect. In stabilization of the enzyme, the organic solvent and the polymer appear to be the primary factors resulting in stabilization. In addition, and in many cases the azide salt aids in increasing stabilization. In either case, it can be observed that both enzymes and coenzymes are still in the same single solution.

Some of the additional reactions which have been performed with the stabilized enzyme and coenzyme compositions are set forth below. The reaction involving the phospholation of creatine is:

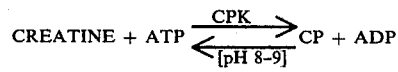

The remaining reactions are all self explanatory with reference to the list of symbols set forth above. For an NADP reaction,

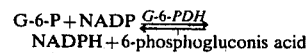

For an ADP reaction,

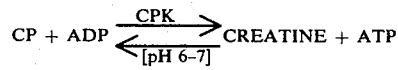

For the following reaction the starting reaction of creatine + ATP would be employed to provide the ADP. Thereafter,

The following reactions show the use of urease and GLDH enzymes in the stabilized liquid compositions.

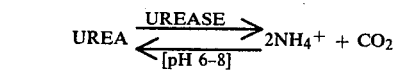

The invention is further illustrated by, but not limited to, the following Examples:

I

About 0.7 grams of a gelatin polymer is added to about 700 milliliters of water. This solution is then heated above 30° C. in order to dissolve the gelatin polymer. After the addition of the polymer, the solution is inserted in a water bath in order to reduce the temperature to about 22° C.

The pH is then adjusted within the range of 6.5 to 8.0. After the temperature has been reduced and pH adjusted, about 2.0 grams of ATP is added to the solution, which is in turn followed by 4.0 grams of NAD. Three grams of a magnesium chloride salt is added along with the NAD. Three hundred ml Glycerol is then added.

After the addition of the glycerol, the pH is adjusted to about 7.5 by the addition of 1 normal hydrochloric acid.

After complete solution is attained, the solution is added to a plastic or glass container, which is then closed. The containers are sealed and stored under refrigeration. It has been found that a stabilized coenzyme composition in this manner provides a storage stability of up to four years without significant degradation.

II

The sample produced in accordance with Example I is provided with the enzyme hexokinase prior to sealing in the glass container. The same shelf life is obtained without significant degradation.

III

The sample of Example II is also provided with the enzyme G-6-PDH prior to sealing in the glass container and the same long shelf life without significant degradation is obtained.

IV

About 1.0 grams of a dextran polymer is added to about 700 milliliters of water. This solution is then heated above 30° C. in order to dissolve the polymer. The solution is inserted in a water bath in order to reduce the temperature to about 22° C.

After the temperature has been reduced, about 2.2 grams of NADP is added to the solution, which is in turn followed by 4.0 grams of ADP. The pH of the solution is adjusted within the range of 6.5 to 8.0. 325 ml glycerol is then added.

After the addition of the glycerol, the pH is adjusted to about 7.5 by the addition of 1 normal hydrochloric acid.

After complete solution is attained, the solution is added to a plastic or glass container, which is then closed. The containers are sealed in an air-tight manner and stored under refrigeration. It has been found that a stabilized coenzyme composition is about as effective as the composition of Example I, even though the azide salt was not added.

The following examples are set forth in schematic form but show the reagents and the amounts added to the various important steps in producing the stabilized compositions of the present invention.

V

Stabilized ADP, AMP and NAD

About 700 ml of water
0.5 grams of gelatin
dissolve with heat
0.7 grams of sodium azide
cool to room temperature
50 grams of creatine phosphate
4 grams of ADP
20 grams of AMP
15 grams of NAD
dissolve and adjust pH between 7 to 9
300 ml glycerol
mix and readjust pH
Package in a bottle and seal.

VI

Stabilized ADP, AMP, NAD, HK and G-6-PDH

About 300 I.U. to about 15,000 I.U. per liter of G-6-PDH and about 100 I.U. to about 10,000 I.U. per liter of HK is added to the solution of Example V prior to packaging thereof.

VII 1.5 grams of NAD
Dissolve in 5 ml water
Add 5 ml of glycerol
Adjust pH to less than 5

VII

Stabilization of NAD and HK 1.5 grams of NAD
Dissolve in 10 ml of pH 7 buffer of 0.1 molar PIPES* buffer
Adjust pH to 6 to 7
Add 10 ml. of glycerol
Readjust pH
Add and dissolve 10 mg. HK of activity of 150 I.U. per miligram.
*PIPES=PIPERAZINE [BIS] ETHANE SULFONIC ACID

IX

Stabilization of creatine, ATP and PEP 1,000 ml of water
Add 12.1 grams of tris(hydroxymethyl)aminomethane
Add 1.0 grams gelatin
Dissolve with heat above 30° C.
Cool to room temperature
Add 2.0 grams ATP
Add 2 grams PEP
Add 10.0 grams creatine
Dissolve and adjust pH to 9

X

To the stabilized solution of Example IX,
100 I.U./liter to 10,000 I.U./liter of LDH was added and 100 I.U./liter to 10,000 I.U./liter of PK was added, prior to packaging.

Each of the compositions of Examples V through X have the same long shelf life without any substantial degradation. Moreover, each of the above examples are based on samples actually prepared and tested in accordance with the present invention.

It is to be realized that only preferred embodiments of the invention have been described and that numerous substitutions, modifications and alterations are permissible without departing from the spirit and scope of the invention as defined in the following claims.

I claim:

1. A stabilized liquid enzyme and coenzyme composition used in biological diagnostic determinations and which enzyme and coenzyme cooperate to affect the reactivity of a biological constituent in a biological diagnostic determination, said enzyme and coenzyme being normally unstable in an aqueous media, said composition comprising:
   (a) at least 30% v/v of an aqueous vehicle,
   (b) at least a sufficient amount of coenzyme to cooperate in a biological diagnostic determination with said enzyme to perform said determination and which coenyme is dissolved in said aqueous vehicle,
   (c) at least 100 I.U. of enzyme dissolved in said aqueous vehicle and being primarily effective in affecting reactivity of said biological constituent and both said enzyme and coenzyme cooperating in a determination reaction,
   (d) a non-reactive aqueous miscible polyol organic solvent present in an amount of about 5% v/v to about 25% V/V in said aqueous vehicle and which solvent is liquid at least at room temperature and dissolved in said aqueous vehicle, the organic solvent being essentially non-degradatively reactive with the enzyme and coenzyme, and where activity of the enzyme and the coenzyme remains substantially unaffected by the presence of the organic solvent in the stabilized composition and in a determination reaction,
   (e) and said composition having a pH from about 6.0 to about 8.5, such that the enzyme and coenzyme are stabilized, said composition being stabilized for a substantial period of time without significant degradation of the enzyme or the coenzyme, and
   (f) said enzyme being selected from the class consisting of glucose-6-phosphate dehydrogenase, hexokinase, glutamate dehydrogenase, creatine phosphokinase, pyruvate kinase and alkali phosphatase, and said coenzyme being selected from the class consisting of nicotinamide-adenine dinucleotide, adenosine triphosphate, adenosine-5'-diphosphate, nicotinamide-adenine dinucleotide phosphate, and adenosine monophosphate.

2. The stabilized liquid composition of claim 1 further characterized in that said composition comprises a first labile coenzyme and at least one second labile coenzyme which are stabilized in said composition.

3. The stabilized liquid composition of claim 1 further characterized in that said composition comprises a water soluble polymer which does not substantially inhibit enzymatic activity.

4. The stabilized liquid composition of claim 3 further characterized in that said composition comprises a first labile enzyme and at least one second labile enzyme which are stabilized in said composition.

5. The stablized liquid composition of claim 1 further characterized in that said composition comprises a bacteriostat which provides stabilization as well as providing bacteriostatic action.

6. The stabilized liquid composition of claim 1 further characterized in that the bacteriostat is an azide compound.

7. The stabilized liquid composition of claim 1 further characterized in that said solvent has the following characteristics:
   (a) pH of 4 to 10
   (b) Liquid at room and refrigerator temperatures;
   (c) Does not react with the coenzymes or enzymes other than forming electrostatic bonds;
   (d) Miscible with water;
   (e) Standard free energy of solvolysis is low.

8. The stablized liquid composition of claim 1 further characterized in that said composition comprises at least two coenzymes and at least two enzymes.

9. A stabilized liquid coenzyme composition used in biological diagnostic determinations which coenzyme is normally unstable in an aqueous media and is capable of cooperating with an enzyme in a biological diagnostic determination, said composition comprising:
   (a) at least 30% V/V of a non-reactive aqueous vehicle,
   (b) at least a sufficient amount of coenzyme to perform a determination dissolved in said aqueous vehicle and in an amount capable of cooperating with an enzyme in a biological diagnostic determination reaction,
   (c) an aqueous miscible polyol organic solvent in an amount of about 5% to about 25% V/V in said aqueous vehicle and which is liquid at least at room temperature and which is dissolved in said aqueous vehicle, and where the organic solvent is essentially non-degradatively reactive with the coenzyme, and where activity of the coenzyme remains substantially unaffected by the presence of the organic solvent in the stabilized composition or in a determination reaction,
   (d) said composition having a pH of from about 6.0 to about 8.5, such that the coenzyme is stabilized, and
   (e) said coenzyme being selected from the class consisting of nicotinamide-adenine dinucleotide, adenosine triphosphate, adenosine-5'-diphosphate, nicotinamide-adenine dinucleotide phosphate, and adenosine monophosphate.

10. The stabilized liquid coenzyme composition of claim 9 further characterized in that said composition comprises a water soluble polymer which does not substantially inhibit coenzyme activity and that said composition also comprises a labile second coenzyme which is stabilized in said composition.

11. The stabilized liquid coenzyme composition of claim 9 further characterized in that said composition comprises a bacteriostat which provides stabilization as well as providing bacteriostatic action.

12. The stabilized liquid coenzyme composition of claim 9 further characterized in that the organic solvent is non-reactive with said coenzyme and aqueous vehicle at room and refrigerator temperatures.

13. The stabilized liquid coenzyme composition of claim 9 further characterized in that the coenzyme is nicotinamide-adenine dinucleotide with a concentration of above 1.2 grams per liter of liquid composition.

14. The stabilized liquid coenzyme composition of claim 9 further characterized in that said organic solvent has the following characteristics:
(a) pH between 4 and 10
(b) Liquid at room and refrigerator temperatures;
(c) Does not react with coenzymes other than forming electrostatic bonds;
(d) Miscible with water;
(e) Standard free energy of solvolysis is low.

15. A stabilized liquid enzyme composition used in biological diagnostic determinations and which enzyme is unstable in an aqueous media, said composition comprising;
(a) at least 30% V/V of an aqueous vehicle,
(b) at least 100 I.U. per liter of enzyme dissolved in said aqueous vehicle and being primarily effective in affecting the reactivity of a biological constituent in a biological diagnostic determination,
(c) a non-reactive aqueous miscible polyol organic solvent present in an amount of about 5% V/V to about 25% V/V in said aqueous vehicle and which solvent is liquid at least at room temperature and dissolved in said vehicle to form a solution with said aqueous vehicle, said organic solvent being essentially non-degradatively reactive with the enzyme, and where activity of the enzyme remains substantially unaffected by the presence of the organic solvent in the stabilized composition or in a biological diagnostic determination reaction,
(d) at least 0.01% of a water soluble polymer in said solution which does not substantially inhibit enzymatic activity,
(e) a bacteriostat which provides stabilization through at least bacteriostatic action,
(f) said composition having a pH of from about 6.0 to about 8.5 such that the enzyme is stabilized, and
(g) said enzyme being selected from the class consisting of glucose-6-phosphate dehydrogenase, hexokinase, glutamate dehydrogenase, creatine phosphokinase, pyruvate kinase and alkali phosphatase.

16. The stabilized liquid enzyme composition of claim 15 further characterized in that said composition comprises a labile second enzyme which is stabilized in said composition.

17. The stabilized liquid enzyme composition of claim 15 further characterized in that the bacteriostat is an azide compound.

18. The stabilized liquid enzyme composition of claim 15 further characterized in that said organic solvent has the following characteristics:
(a) pH between 4 to 10
(b) Liquid at room and refrigerator temperatures;
(c) Does not react with enzymes other than forming electrostatic bonds;
(d) Miscible with water;
(e) Standard free energy of solvolysis is low.

19. The stabilized liquid enzyme composition of claim 18 further characterized in that said organic solvent is non-reactive with said enzyme and aqueous vehicle at room and refrigerator temperatures.

20. A method of stabilizing a composition containing labile coenzyme and labile enzyme used in biological diagnostic determinations and which enzyme and coenzyme cooperate to affect the reactivity of a biological constituent in a biological diagnostic determination, said enzyme and coenzyme being normally unstable in aqueous media, said method comprising:
(a) mixing at least 30% V/V of water with an aqueous miscible non-reactive polyol organic solvent to form an aqueous miscible organic solvent solution, where the organic solvent is present in an amount of about 5% V/V to about 25% V/V in the solution, and which organic solvent is liquid at least at room temperature and dissolved in the solution,
(b) introducing a polymer in the aqueous miscible organic solvent solution,
(c) adding at least a sufficient amount per liter of a labile coenzyme to said solution to perform a determination and which coenzyme is dissolved in said solution and cooperates with an enzyme in a determination reaction, the activity of said coenzyme remaining unaffected by the presence of the organic solvent in the stabilized composition or in a determination reaction,
(d) adjusting the pH to within the range of 6.0 to 8.5, such that the coenzyme is stabilized,
(e) adding at least 100 I.U. per liter of a labile enzyme to said solution, which enzyme is dissolved in said solution and cooperates in a determination reaction, said organic solvent being essentially non-degradatively reactive with the enzyme and coenzyme, and where activity of the enzyme and the coenzyme remains substantially unaffected by the presence of the organic solvent in the stabilized composition or in a biological diagnostic determination reaction, and
(f) sealing the composition, said composition being stabilized for a substantial period of time without significant degradation of the enzyme and the coenzyme, and
(g) said enzyme being selected from the class consisting of glucose-6-phosphate dehydrogenase, hexokinase, glutamate dehydrogenase, creatine phosphokinase, pyruvate kinase and alkali phosphatase, and said coenzyme being selected from the class consisting of nicotinamide-adenine dinucleotide, adenosine triphosphate, adenosine-5'-diphosphate, nicotinamide-adenine dinucleotide phosphate, and adenosine monophosphate.

21. The method of claim 20 further characterized in that said method comprises adding a bacteriostatic agent which also functions as an enzyme stabilizing agent.

22. The method of claim 21 further characterized in that said bacteriostatic agent is an azide compound.

23. The method of claim 20 further characterized in that said method also comprises adding a second coenzyme to said solution which is also stabilized therein.

24. The method of claim 20 further characterized in that said method also comprises adding a second enzyme to said solution which is also stabilized therein, after adjustment of the pH.

25. The method of claim 20 further characterized in that said solvent has the following characteristics:
(a) pH between 4 to 10
(b) Liquid at room and refrigerator temperatures;
(c) Does not react with the enzymes or coenzymes other than forming electrostatic bonds;
(d) Miscible with water;
(e) Standard free energy of solvolysis is low.

26. The method of claim 25 further characterized in that the organic solvent contains 2-4 hydroxyl groups and 2-10 carbon atoms.

27. The method of claim 20 further characterized in that said polymer is present in an amount of at least 0.01%.

28. A method of stabilizing a labile coenzyme containing composition used in biological diagnostic determinations and which coenzyme is normally unstable in an aqueous media and cooperates with an enzyme in the biological diagnostic determinations, said method comprising:
   (a) dissolving a coenzyme in an aqueous base in an amount sufficient to perform a determination and which coenzyme cooperates with an enzyme in a biological diagnostic determination reaction,
   (b) mixing said coenzyme containing aqueous base with about 5% to about 25% V/V of a non-reactive aqueous miscible polyol organic solvent to provide a stabilized composition containing at least 30% V/V of aqueous base and which solvent is liquid at least at room temperature and dissolved in the aqueous base, and where the organic solvent is essentially non-degradatively reactive with the coenzyme, and where activity of the coenzyme remains substantially unaffected by the presence of the organic solvent in the stabilized composition or in a determination reaction,
   (c) adjusting the composition pH to about 6.0 to about 8.5, such that the coenzyme is stabilized,
   (d) said coenzyme being selected from the class consisting of nicotinamide-adenine dinucleotide, adenosine triphosphate, adenosine-5'-diphosphate, creatine phosphokinase, nicotinamide-adenine dinucleotide phosphate, and adenosine monophosphate, and
   (e) sealing the composition in a container.

29. The method of claim 28 further characterized in that said method comprises dissolving a water soluble polymer in said composition which does not substantially inhibit coenzyme activity.

30. The method of claim 28 further characterized in that said method also comprises adding a second coenzyme to said solution which is also stabilized therein.

31. The method of claim 28 further characterized in that said solvent has the following characteristics:
   (a) pH between 4 to 10
   (b) Liquid at room and refrigerator temperatures;
   (c) Does not rect with coenzymes other than forming electrostatic bonds;
   (d) Miscible with water;
   (e) Standard free energy of solvolysis is low.

32. The method of claim 31 further characterized in that the solvent contains from 2-10 carbon atoms and 2-4 hydroxyl groups.

33. The method of claim 29 further characterized in that the polymer is gelatin present in said solution in an amount of at least 0.01%.

34. A method of stabilizing a labile enzyme used in biological diagnostic determinations and which enzyme is normally unstable in an aqueous media, said method comprising:
   (a) mixing at least 30% V/V of water with an aqueous miscible polyol organic solvent to form a solution thereof and which organic solvent is liquid at least at room temperature and dissolved in the water, such that the solvent is present from about 5% V/V to about 25% V/V,
   (b) adding at least 0.01% of water soluble polymer to said solution,
   (c) adding a bacteriostatic agent which also stabilizes the enzyme in said solution through at least bacteriostatic action,
   (d) dissolving at least 100 I.U. per liter of enzyme in said solution to form the composition, and which enzyme is primarily effective in affecting the reactivity of a biological constituent in a biological diagnostic determination, said solvent being essentially non-degradatively reactive with the enzyme, and where activity of the enzyme remains substantially unaffected by the presence of the organic solvent in the stabilized composition or in a biological diagnostic determination reaction,
   (e) said enzyme being selected from the class consisting of glucose-6-phosphate dehydrogenase, hexokinase, glutamate, dehydrogenase, creatine phosphokinase, pyruvate kinase and alkali phosphatase,
   (f) and sealing the composition.

35. The method of claim 34 further characterized in that said bacteriostatic agent is an azide compound.

36. The method of claim 34 further characterized in that said method also comprises adding a second enzyme to said solution which is also stabilized therein.

37. The method of claim 34 further characterized in that said solvent has the following characteristics:
   (a) pH between 4 to 10
   (b) Liquid at room and refrigerator temperatures;
   (c) Does not react with coenzymes other than forming electrostatic bonds;
   (d) Miscible with water;
   (e) Standard free energy of solvolysis is low.

38. The method of claim 37 further characterized in that the solvent contains from 2-10 carbon atoms and 2-4 hydroxyl groups.

39. The method of claim 34 further characterized in that the polymer is gelatin present in said solution in an amount from about 0.01% to about 0.5%.

40. A stabilized liquid enzyme and coenzyme composition used in biological diagnostic determinations of creatine phosphokinase and glucose and which enzyme and coenzyme cooperate to affect the reactivity of a biological constituent in a determination of creatine phosphokinase or glucose, said enzyme and coenzyme being normally unstable in an aqueous media, said composition comprising:
   (a) at least 30% V/V of an aqueous vehicle,
   (b) at least a sufficient amount of coenzyme selected from the class consisting of nicotinamide-adenine dinucleotide, nicotinamide-adenine dinucleotide reduced, and nicotinamide-adenine dinucleotide phosphate and a coenzyme selected from the class consisting of adenosine-5'-diphosphate, adenosine monophosphate and adenosine triphosphate to perform a determination of creatine phosphokinase or glucose, said coenzymes cooperating with said enzyme in a biological diagnostic determination of creatine phosphokinase or glucose and being dissolved in said aqueous vehicle,
   (c) at least 100 I.U. of enzyme selected from the class consisting of glucose-6-phosphate dehydrogenase and kexokinase dissolved in said aqueous vehicle and both said enzyme and coenzyme cooperating in a determination reaction,
   (d) a non-reactive polyol organic solvent in an amount of about 5% V/V to about 25% V/V in said aqueous vehicle and which is liquid at least at room temperature and dissolved in said aqueous vehicle, said organic solvent being essentially non-degradatively reactive with the enzyme and coenzymes, and where activity of the enzyme and the coenzymes remains substantially unaffected by the presence of the organic solvent in the stabilized composition or in a determination reaction, (e) a water soluble polymer in said vehicle which does not substantially inhibit enzymatic activity, (f) and said composition having a pH from about 6.0 to about 8.5, such that the enzymes and coenzymes are stabilized, said composition being stabilized for a substantial period of time without significant degradation of the enzyme and the coenzymes.

41. The stabilized liquid composition of claim 40 further characterized in that said polymer is selected from the class consisting of polyvinylpyrrolidine, dextran and gelatin.

42. The stabilized liquid composition of claim 40 further characterized in that said solvent has the following characteristics:
 (a) pH of 4 to 10
 (b) Liquid at room and refrigerator temperatures;
 (c) Does not react with the coenzymes or enzymes other than forming electrostatic bonds;
 (d) Miscible with water;
 (e) Standard free energy of solvolysis is low.

43. The stabilized liquid composition of claim 42 further characterized in that the solvent contains from 2-10 carbon atoms and 2-4 hydroxyl groups.

44. The stabilized liquid composition of claim 40 further characterized in that the polymer is gelatin present in said solution in an amount of at least 0.01%.

45. A stabilized liquid coenzyme composition used in biological diagnostic determinations of creatine phosphokinase or glucose and which coenzyme cooperates with an enzyme in the biological diagnostic determination and is normally unstable in an aqueous media, said composition comprising:
 (a) at least 30% V/V of a non-reactive aqueous vehicle,
 (b) at least a sufficient amount of a coenzyme selected from the class consisting of nicotinamide-adenine dinucleotide, nicotinamide-adenine dinucleotide reduced, and nicotinamide-adenine dinucleotide phosphate and a coenzyme selected from the class consisting of adenosine-5'-diphosphate, adenosine monophosphate and adenosine triphosphate to perform a determination of creatine phosphokinase or glucose, said coenzymes cooperating with said enzyme in a biological diagnostic determination of creatine phosphokinase or glucose and being dissolved in said aqueous vehicle,
 (c) a non-reactive aqueous miscible polyol organic solvent present in an amount of about 5% V/V to about 25% V/V in said aqueous vehicle and which is liquid at least at room temperature and dissolved in said aqueous vehicle, said polyol being essentially non-degradatively reactive with the coenzymes, and where the activity of the coenzymes remains substantially unaffected by the presence of the organic solvent in the stabilized composition or in a determination reaction, and
 (d) said composition having a pH of from about 6.0 to about 8.5, such that the coenzyme is stabilized.

46. The stabilized liquid coenzyme composition of claim 45 further characterized in that said composition comprises a water soluble polymer which does not substantially inhibit coenzymic activity, and said polymer being selected from the class consisting of polyvinylpyrrolidone, dextran and gelatin.

47. The stabilized liquid coenzyme composition of claim 46 further characterized in that said composition also comprises a labile first enzyme and a labile second enzyme which are stabilized in said composition.

48. The stabilized liquid coenzyme composition of claim 45 further characterized in that said solvent has the following characteristics:
 (a) pH of 4 to 10
 (b) Liquid at room and refrigerator temperatures;
 (c) Does not react with the coenzymes or enzymes other than forming electrostatic bonds;
 (d) Miscible with water;
 (e) Standard free energy of solvolysis is low.

49. A method of stabilizing a liquid enzyme and coenzyme composition used in biological diagnostic determinations of creatine phosphokinase or glucose and which enzyme and coenzyme cooperate to affect the reactivity of a biological constituent in a determination of creatine phosphokinase and glucose, said enzyme and coenzyme being normally unstable in an aqueous media, said method comprising:
 (a) mixing at least 30% V/V of water with about 5% to about 25% V/V of an aqueous miscible polyol organic solvent to form a mixture of organic solvent and water with the organic solvent dissolved in the water,
 (b) dissolving in said mixture at least a sufficient amount of coenzyme, nicotinamide-adenine dinucleotide or nicotinamide-adenine dinucleotide reduced or nicotinamide-adenine dinucleotide phosphate to perform a determination,
 (c) dissolving in said mixture a sufficient amount of coenzymic, adenosine monophosphate or adenosine-5'-diphosphate or adenosine triphosphate to cooperate in a determination of creatine phosphokinase or glucose,
 (d) adjusting the pH to within the range of about 6.0 to about 8.5 such that the coenzymes are stabilized,
 (e) dissolving in said mixture at least 100 I.U. per liter of enzyme hexokinase and at least 100 I.U. per liter of enzyme glucose-6-phosphate dehydrogenase and both said enzymes and coenzymes cooperating in a determination reaction of creatine phosphokinase or glucose, and
 (f) said organic solvent being essentially non-degradatively reactive with the enzymes and coenzymes, and where activity of the enzymes and coenzymes remains substantially unaffected by the presence of the organic solvent in the stabilized composition or in a determination reaction, and
 (g) sealing said composition, said composition being stabilized for a substantial period of time without significant degradation of the enzymes and the coenzymes.

50. The method of stabilizing the liquid composition of claim 49 further characterized in that said method comprises dissolving in said vehicle a water soluble polymer which does not substantially inhibit enzymatic activity.

51. The method of stabilizing the liquid composition of claim 49 further characterized in that said method comprises dissolving in said vehicle a bacteriostat which provides stabilization as well as providing bacteriostatic action.

52. The method of stabilizing the liquid composition of claim 49 further characterized in that said solvent has the following characteristics:
(a) pH of 4 to 10
(b) Liquid at room and refrigerator temperatures;
(c) Does not react with the coenzymes and enzymes other than forming electrostatic bonds;
(d) Miscible with water;
(e) Standard free energy of solvolysis is low.

53. A stabilized liquid enzyme composition used in biological diagnostic determinations of creatine phosphokinase or glucose and which enzyme is unstable in an aqueous media, said composition comprising:
(a) at least 30% V/V of an aqueous vehicle,
(b) at least 100 I.U. per liter of enzyme hexokinase dissolved in said aqueous vehicle,
(c) at least 100 I.U. per liter of enzyme glucose-6-phosphate dehydrogenase dissolved in said aqueous vehicle,
(d) a non-reactive aqueous miscible polyol organic solvent present in an amount of about 5% to about 25% V/V in said aqueous vehicle and which is liquid at least at room temperature and dissolved in said aqueous vehicle to form a solution with said aqueous vehicle, said organic solvent being essentially non-degradatively reactive with the enzymes and where activity of the enzymes remain substantially unaffected by the presence of the organic solvent in the stabilized composition or in a biological diagnostic determination reaction,
(e) at least 0.01% of a water soluble polymer in said solution which does not substantially inhibit enzymatic activity,
(f) a bacteriostat which provides stabilization through at least bacteriostatic action, and
(g) said composition having a pH of from about 6.0 to about 8.5 such that the enzyme is stabilized.

54. The stabilized liquid enzyme composition of claim 53 further characterized in that said organic solvent is non-reactive with said enzyme and aqueous vehicle at room and refrigerator temperatures.

55. The stabilized liquid composition of claim 53 further characterized in that the bacteriostat is an azide compound.

56. The stabilized liquid enzyme composition of claim 53 further characterized in that said solvent has the following characteristics:
(a) pH of 4 to 10
(b) Liquid at room and refrigerator temperatures;
(c) Does not react with the coenzymes or enzymes other than forming electrostatic bonds;
(d) Miscible with water;
(e) Standard free energy of solvolysis is low.

57. A method of stabilizing a labile coenzyme containing composition used in biological determinations of creatine phosphokinase or glucose and which coenzyme is unstable in an aqueous media and cooperates with an enzyme in the biological diagnostic determinations, said method comprising:
(a) providing at least 30% V/V of an aqueous vehicle,
(b) dissolving in said aqueous vehicle a coenzyme selected from the class consisting of nicotinamide-adenine dinucleotide, nicotinamide-adenine dinucleotide reduced, and nicotinamide-adenine dinucleotide phosphate in an amount sufficient to perform a determination of creatine phosphokinase or glucose,
(c) dissolving in said aqueous vehicle a coenzyme selected from the class consisting of adenosine-5'-diphosphate, adenosine monophosphate and adenosine triphosphate in an amount sufficient to perform a determination of creatine phospholinase or glucose, said coenzymes cooperating with an enzyme in a biological diagnostic determination of creatine phosphokinase or glucose,
(d) dissolving a non-reactive aqueous miscible polyol organic solvent in an amount of about 5% to about 25% V/V in said aqueous vehicle and which solvent is liquid at least at room temperature, said organic solvent being essentially non-degradatively reactive with the coenzymes, and where activity of the coenzymes remains substantially unaffected by the presence of the organic solvent in the stabilized composition or in a biological diagnostic determination reaction,
(e) adjusting the pH of the composition to about 6.0 to about 8.5 such that the coenzymes are stabilized, and
(f) sealing the composition in a container.

58. The method of claim 57 further characterized in that said organic solvent is non-reactive with said coenzyme and aqueous vehicle at room and refrigerator temperatures.

59. The method of claim 57 further characterized in that said composition comprises a labile enzyme which is stabilized in said composition.

60. The method of claim 59 further characterized in that the enzyme is selected from the class consisting of glucose-6-phosphate dehydrogenase and hexokinase.

61. The method of claim 57 further characterized in that said organic solvent has the following characteristics:
(a) pH of 4 to 10
(b) Liquid at room and refrigerator temperatures;
(c) Does not react with the coenzymes or enzymes other than forming electrostatic bonds;
(d) Miscible with water;
(e) Standard free energy of solvolysis is low.

62. A method of stabilizing a labile enzyme composition used in biological diagnostic determinations of creatine phosphokinase or glucose and which enzyme is normally unstable in an aqueous media, said method comprising:
(a) mixing at least 30% V/V of water with about 5% to about 25% V/V of an aqueous miscible polyol organic solvent to form a solution thereof so that the solvent is dissolved in the water and which organic solvent is liquid at least at room temperature,
(b) adding at least 0.01% of a water soluble polymer to said solution and which does not substantially inhibit enzymatic activity,
(c) adding a bacteriostatic agent which also functions as an enzyme stabilizing agent to said solution,
(d) dissolving at least 100 I.U. per liter of the enzyme hexokinase in said solution to form the composition, and which enzyme cooperates in a determination reaction of creatine phosphokinase or glucose,
(e) dissolving at least 100 I.U. per liter of the enzyme glucose-6-phosphate dehydrogenase and which latter enzyme also cooperates in a determination of creatine phosphokinase or glucose,
(f) and sealing the composition.

63. The method of claim 62 further characterized in that said bacteriostatic agent is an azide compound.

64. The method of claim 62 further characterized in that said method also comprises adding a coenzyme to said solution which is also stabilized therein.

65. The method of claim 62 further characterized in that said solvent has the following characteristics:
 (a) pH between 4 to 10;
 (b) Liquid at room and refrigerator temperatures;
 (c) Does not react with the enzymes other than forming electrostatic bonds;
 (d) Miscible with water;
 (e) Standard free energy of solvolysis is low.

66. The method of claim 65 further characterized in that the solvent contains from 2-10 carbon atoms and 2-4 hydroxyl groups.

67. The method of claim 62 further characterized in that the polymer is gelatin present in said solution in an amount from about 0.01% to about 0.5%.

* * * * *